US 6,540,782 B1

(12) United States Patent
Snyders (10) Patent No.: US 6,540,782 B1
(45) Date of Patent: Apr. 1, 2003

(54) ARTIFICIAL HEART VALVE (76) Inventor: Robert V. Snyders, 1638 Wolf Trail Rd., Ballwin, MO (US) 63021

( * ) Notice: Subject to any disclaimer, the term of this patent is extended or adjusted under 35 U.S.C. 154(b) by 9 days.

(21) Appl. No.: 09/775,360

(22) Filed: Feb. 1, 2001

Related U.S. Application Data (60) Provisional application No. 60/179,853, filed on Feb. 2, 2000.

(51) Int. Cl.$^7$ .................................................. A61F 2/06
(52) U.S. Cl. ...................................... 623/2.14; 623/2.11
(58) Field of Search ................................ 623/2.1, 2.11, 623/2.12, 2.13, 2.14, 2.17, 2.18, 2.33, 2.35

(56) References Cited

U.S. PATENT DOCUMENTS

| 4,339,831 | A | * | 7/1982 | Johnson | 137/512.15 |
| 5,332,402 | A | * | 7/1994 | Teitelbaum | 623/2.35 |
| 5,397,351 | A | | 3/1995 | Pavcnik et al. | |
| 5,411,552 | A | | 5/1995 | Andersen et al. | |
| 5,413,599 | A | | 5/1995 | Imachi et al. | |
| 5,545,214 | A | * | 8/1996 | Stevens | 128/898 |
| 5,855,601 | A | | 1/1999 | Bessler et al. | |
| 5,861,028 | A | * | 1/1999 | Angell | 623/2.11 |

FOREIGN PATENT DOCUMENTS

| DE | 41 01 935 A 1 | 7/1992 |
| WO | WO 99/13801 | 3/1999 |

OTHER PUBLICATIONS

H.R. Andersen, et al., *Transluminal Implantation of Articial Heart Valves. Description of a New Expandable Aortic Valve and Initial Results with Implantation by Catheter Technique in Closed Chest Pigs*, 13 European Heart Journal 704–708 (1992).

Steven R. Bailey, *Percutaneous Expandable Prosthetic Valves*, Textbook of Interventional Cardiology 1268–76 (1995).

Dwight E. Harken, et al., *Partial and Complete Prostheses in Aortic Insufficiency*, 40 J. Thoracic and Cardiovas. Surg. 744–62 (1960).

Stephen L. Hilbert, et al., *Evaluation of Explanted Polyurethane Trileaflet Cardiac Valve Prostheses*, 94 J. Thorac Cardiovasc Surg 419–29 (1987).

(List continued on next page.)

Primary Examiner—Corrine McDermott
Assistant Examiner—William H Matthews
(74) Attorney, Agent, or Firm—Sonnenschein Nath & Rosenthal (57) ABSTRACT An artificial valve for repairing a damaged heart valve having a plurality of cusps separating an upstream region from a downstream region. The artificial valve includes a flexibly resilient frame sized and shaped for insertion in a position between the upstream region and the downstream region. The frame has a plurality of peripheral anchors for anchoring the frame in the position between the upstream region and the downstream region and a central portion located between the plurality of peripheral anchors. The valve also includes a flexible valve element attached to the frame and to the central portion of the frame having an upstream side facing the upstream region when the frame is anchored in the position between the upstream region and the downstream region and a downstream side opposite the upstream side facing the downstream region when the frame is anchored in the position between the upstream region and the downstream region. The valve element moves to an open position when fluid pressure in the upstream region is greater than fluid pressure in the downstream region to permit downstream flow from the upstream region to the downstream region. The valve element moves to a closed position when fluid pressure in the downstream region is greater than fluid pressure in the upstream region to prevent flow reversal from the downstream region to the upstream region.

30 Claims, 4 Drawing Sheets

OTHER PUBLICATIONS

Charles A. Hufnagel, *Basic Concepts in the Development of Cardiovascular Prostheses*, 137 Great Ideas in Surgery 285–300 (Mar. 1979).

L.L. Knudsen, et al., *Catheter–implanted Prosthetic Heart Valves* 18 The International Journal of Artificial Organs 253–262 (1993).

H.B. Lo, et al., *A Tricuspid Polyurethane Heart Valve as an Alternative to Mechanical Prostheses or Bioprostheses*, XXXIV Trans. Am. Soc. Artif. Intern. Organs 839–44 (1988).

St. Jude Medical Heart Valve Division, *The Right Choice for all the Right Reasons*, (1999).

* cited by examiner

ARTIFICIAL HEART VALVE

CROSS-REFERENCE TO RELATED APPLICATION

This application claims benefit of Provisional Patent Application No. 60/179,853 filed Feb. 2, 2000, which is hereby incorporated by reference.

BACKGROUND OF THE INVENTION

The present invention relates generally to valve implants, and more particularly to artificial heart valves for repairing damaged heart valves.

A human heart has four chambers which alternately expand and contract to pump blood through the vessels of the body. The heart also includes a check valve at the upstream end of each chamber to ensure that blood flows in the correct direction through the body as the heart chambers expand and contract. These valves sometimes become damaged resulting in their inability to close when the downstream chamber contracts. When the valves do not close, blood flows backward through the valve resulting in diminished blood flow and lower blood pressure. The valves can also become damaged so they do not open sufficiently thereby resulting in diminished downstream blood flow.

Although replacement valves and surgical procedures have been developed to alleviate these conditions, they have significant drawbacks. Many earlier valves require invasive implantation techniques in which the chest is opened, the ribs are spread, the heart is paralyzed, and following cardio-pulmonary bypass, the heart is cut open to implant the valve. These invasive techniques are stressful on the patient, increase the opportunity for infection and slow recovery. As a result, valves which may be implanted with non-invasive techniques have been developed. These valves are implanted by transluminal or endothoracoscopic techniques which reduce many of the drawbacks associated with invasive surgery. However, many of these valves also require the damaged native heart valve be removed prior to implanting the artificial valve. Removing the native valve increases the risk that a portion of the valve will migrate through the body and block vessels downstream from the heart.

Many mechanical and bioprosthetic valves have been developed to replace native heart valves. See C. A. Hufnagel, *Basic Concepts in the Development of Cardiovascular Prostheses*, 137 Am. J. of Surg. at 285–300 (1972). See also D. E. Harken et al., *Partial and Complete Prosthesis in Aortic Insufficiency*, 40 J. Thorac & Cdvsc Surg., no. 6., at 744–62 (1960). These valves include ball-valve prostheses, flap-valve prostheses, polymeric trileaflet synthetic valves, and bioprosthetic valves made from animal allograft tissues such as pig valves and preserved heterologous bovine and porcine pericardial tissue valves. See H. B. Lo et al., *A Tricuspid Polyurethane Heart Valve as an Alternative to Mechanical Prostheses or Bioprostheses*, 34 Trans. Am. Soc. of Art. Int. Organs at 839–44 (1988); and S. L. Hilbert et al., *Evaluation of Explanted Polyurethane Trileaflet Cardiac Valve Prostheses*, 94 J. Thorac & Cdvsc Surg. at 419–29 (1987). Most of the aforementioned valves require open chest surgery and cardio-pulmonary bypass for implantation.

More recently percutaneous and transluminal implantation have been suggested. See Steven R. Bailey, *Percutaneous Expandable Prosthetic Valves* Textbook of Interventional Cardiology, chap. 75 (1995) (referencing work of Andersen et al.) See also Knudsen et al., *Catheter-implanted Prosthetic Heart Valves*, 6 Int'l J. of Art. Organs, no. 5, at 253–62 (1993); Knudsen et al. *Transluminal Implantation of Artificial Heart Valves. Description of New Expandable Aortic Valve and Initial Results With Implantation by Catheter Technique in Closed Chest Pigs*, 13 European Heart J. at 704–08 (1992); and U.S. Pat. No. 5,411,552 (Andersen). The Andersen device includes a heterologous pig valve mounted in an annular ring. Due to the size of this device, it must be implanted by direct abdominal aortic incision and entry. Further, the Andersen device requires a separate inflating balloon for its deployment. U.S. Pat. No. 5,397,351 (Pavcnik) describes an expandable caged poppet for percutaeuous implantation in an aortic valve site. However, the size of the Pavcnik device makes percutaneous implantation difficult. U.S. Pat. No. 5,885,601 (Bessler) describes a transluminal valve implantation but does not describe the specific valve construction. The Bessler procedure includes excision, vacuum removal of the native valve, cardio-pulmonary bypass and backflushing of the coronary arterial tree.

SUMMARY OF THE INVENTION

Among the several objects and features of the present invention may be noted the provision of an artificial heart valve which accommodates implantation without removing the damaged native heart valve; the provision of a valve which may be implanted using non-invasive surgery; the provision of a valve which permits implantation without the need for cardio-pulmonary bypass; and the provision of a valve which permits implantation by conventional open chest surgery and cardio-pulmonary bypass.

Briefly, apparatus of this invention is an artificial valve for repairing a damaged heart valve having a plurality of cusps separating an upstream region from a downstream region. The artificial valve comprises a flexibly resilient frame sized and shaped for insertion in a position between the upstream region and the downstream region. The frame has a plurality of peripheral anchors for anchoring the frame in the position between the upstream region and the downstream region and a central portion located between the anchors. In addition, the artificial valve includes a flexible valve element attached to the frame and to the central portion of the frame. The valve element has an upstream side facing the upstream region when the frame is anchored in the position between the upstream region and the downstream region and a downstream side opposite the upstream side facing the downstream region when the frame is anchored in the position between the upstream region and the downstream region. The valve element moves in response to a difference between fluid pressure in the upstream region and fluid pressure in the downstream region between an open position in which the element permits downstream flow between the upstream region and the downstream region and a closed position in which the element blocks flow reversal from the downstream region to the upstream region. The valve element moves to the open position when fluid pressure in the upstream region is greater than fluid pressure in the downstream region to permit downstream flow from the upstream region to the downstream region, and the valve element moves to the closed position when fluid pressure in the downstream region is greater than fluid pressure in the upstream region to prevent flow reversal from the downstream region to the upstream region.

In another aspect of the invention, the artificial valve comprises a flexibly resilient frame and a flexible valve element attached to the frame. The valve element has a convex upstream side facing the upstream region when the frame is anchored in the position between the upstream region and the downstream region and a concave downstream side opposite the upstream side facing the downstream region when the frame is anchored in the position between the upstream region and the downstream region. The valve element moves in response to a difference between fluid pressure in the upstream region and the downstream region between an open position and a closed position.

In yet another aspect of the present invention, the artificial valve comprises a plurality of U-shaped frame elements sized and shaped for insertion in the heart in the position between the upstream region and the downstream region. Each of the plurality of frame elements has opposite ends. The elements are joined together generally midway between their respective ends at a junction of the elements. In addition, the artificial valve includes a band extending between each frame element and an adjacent frame element to limit spacing between the frame elements. Further, the artificial valve includes a flexible valve element attached to the junction of the frame elements. The valve element has a convex upstream side facing the upstream region when the frame elements are inserted in the position between the upstream region and the downstream region and a concave downstream side opposite the upstream side facing the downstream region when the frame elements are inserted in the position between the upstream region and the downstream region. The valve element moves in response to a difference between fluid pressure in the upstream region and fluid pressure in the downstream region between an open position and a closed position.

In still another aspect, the invention includes the artificial valves described above having a frame which is collapsible to a configuration having a maximum width less than about 18 mm in combination with an instrument for inserting the artificial valve in the position between the upstream region and the downstream region. The instrument includes a holder having a hollow interior sized for holding the artificial valve when the frame is in the collapsed configuration. In addition, the instrument includes an elongate manipulator attached to the holder for manipulating the holder into position between the upstream region and the downstream region and an ejector mounted in the hollow interior of the holder for ejecting the artificial heart valve from the hollow interior of the holder into position between the upstream region and the downstream region.

Still further, the invention includes an endothoracoscopic method of inserting an artificial valve between a plurality of cusps of a damaged heart valve. The method comprises the steps of making an opening in a chest wall, making an incision in a heart and inserting an end of an elongate instrument through the opening made in the chest wall and incision made in the heart. In addition, the method includes positioning the inserted end of the instrument adjacent the cusps of the damaged heart valve and ejecting an artificial valve from the end of the instrument into a position between the cusps of the damaged heart valve without removing the damaged heart valve from the heart.

Moreover, the invention includes a transluminal method of inserting an artificial valve between a plurality of cusps of a damaged heart valve comprising the steps of making an incision in a vessel leading to the heart and inserting an end of an elongate flexible instrument through the incision made in the vessel. In addition, the method includes pushing the end of the instrument through the vessel until the end is adjacent the cusps of the damaged heart valve and ejecting an artificial valve from the end of the instrument into a position between the cusps of the damaged heart valve without removing the damaged heart valve from the heart.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
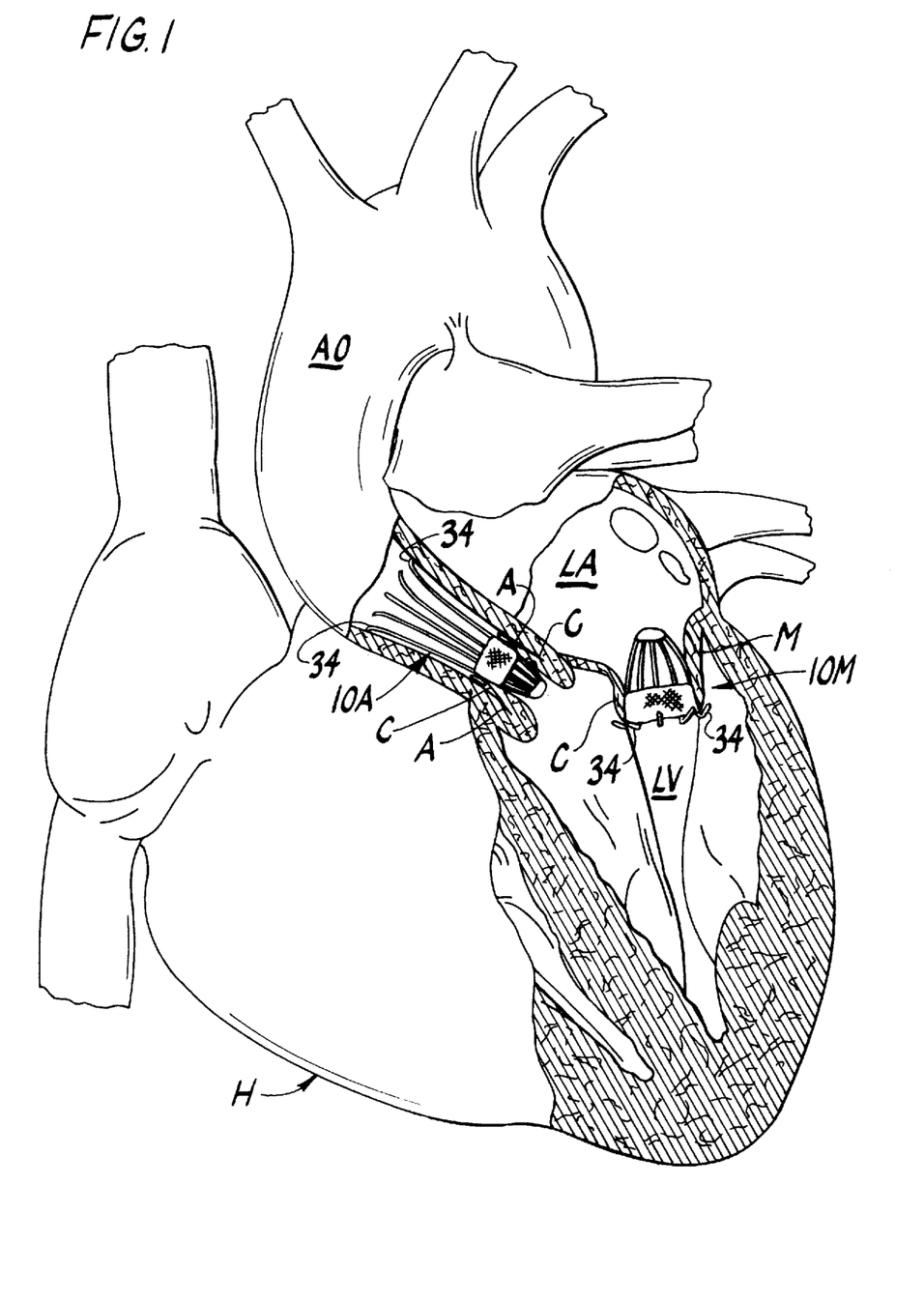
FIG. 1 is a front elevation of a heart in partial section showing two artificial valves of the present invention.

Referring now to the drawings and in particular to FIG. 1, artificial heart valves of the present invention are designated in their entireties by the reference numbers 10A and 10M. The artificial valve 10A is specifically configured for repairing a damaged aortic valve A of a heart, generally designated by H. The artificial valve 10M is specifically configured for repairing a damaged mitral valve M. In addition, an artificial valve having a configuration similar to valve 10A may be used to repair a damaged pulmonary heart valve (not shown), and a valve having a configuration similar to valve 10M may be used to repair a damaged tricuspid heart valve (not shown). Each native heart valve (e.g., mitral valve M) normally has two cusps C (or three cusps in the case of the tricuspid valve) separating an upstream region (e.g., the left atrium LA) of the heart H from a downstream region (e.g., the left ventricle LV) of the heart positioned downstream from the upstream region. In use, the artificial heart valves (e.g., the artificial heart valve 10M) are positioned between the upstream region and the downstream region, preferably between the cusps C of the respective native valve (e.g., the mitral valve M), to ensure blood flows through the heart H in the appropriate direction as will be explained in greater detail below.

Figure 2:
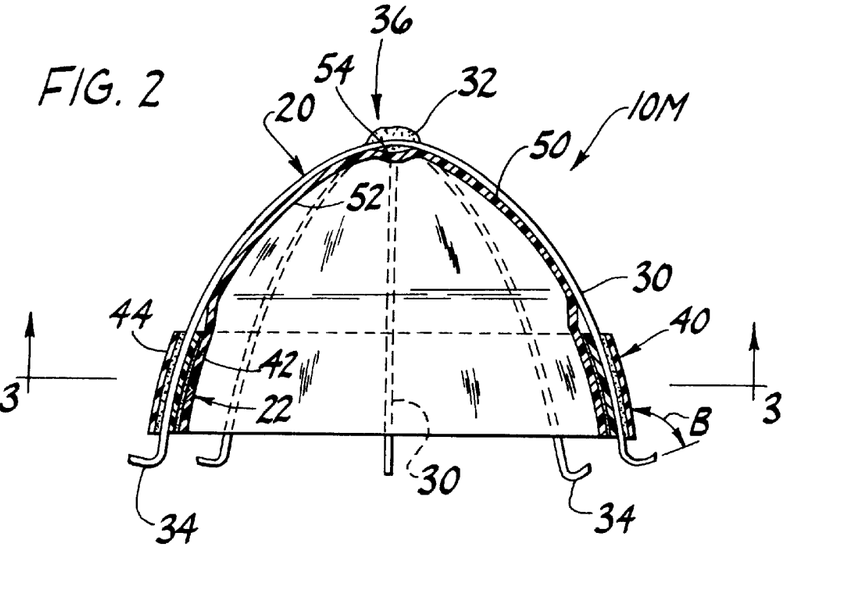
FIG. 2 is a vertical cross section of an artificial valve.
Figure 3:
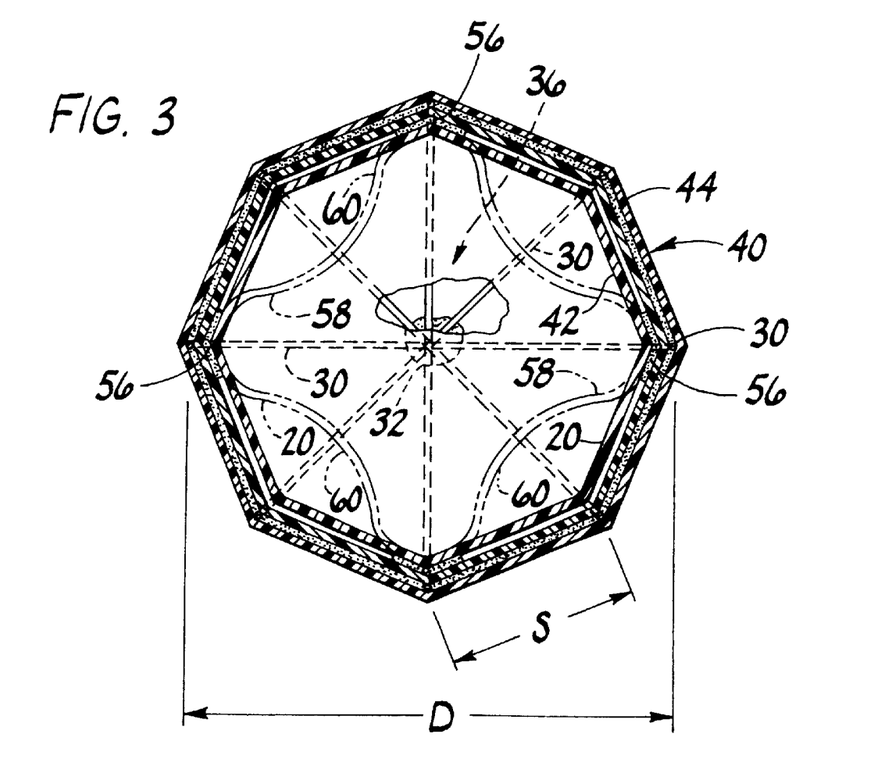
FIG. 3 is a cross section of the valve taken in the plane of line 3—3 of FIG. 2.
Figure 4:
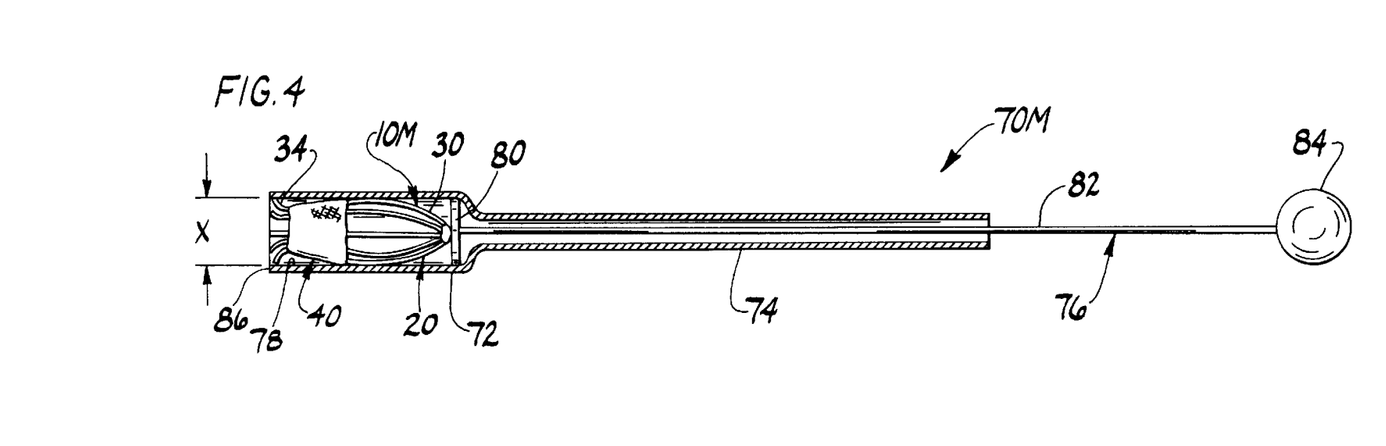
FIG. 4 is a vertical cross section of an instrument for implanting a valve using an endothoracoscopic procedure of the present invention.

As illustrated in FIG. 2, the artificial valve 10M comprises a flexibly resilient external frame, generally designated by 20, and a flexible valve element, generally designated by 22. The frame 20 includes a plurality of U-shaped stenting elements 30. Each of the U-shaped elements 30 has a length extending between opposite ends. Although the elements 30 may have other lengths without departing from the scope of the present invention, the elements of the preferred embodiment have approximately equal lengths. Further, the elements 30 are joined generally midway between their respective ends at a junction 32 of the elements. Although four frame elements 30 are shown in FIGS. 2 and 3, the valve 10M may have fewer or more elements without departing from the scope of the present invention. Preferably, the stenting elements 30 are sufficiently compressible to permit the valve 10M to be compressed to a configuration such as shown in FIG. 4 during implantation in the respective heart valve as will be explained below. Still further, the stenting elements 30 preferably are sufficiently resilient to hold the artificial valve 10M in position between the cusps C of the native valve M after implantation and to hold the cusps of the native valve open. As used herein, the term "stenting" is intended to convey that the element 30 holds the cusps of the native valve at least partially open. Moreover, although the elements 30 of the preferred embodiment are made of nickel alloy wire such as nitinol wire, other materials may be made without departing from the scope of the present invention. Further, although the wire of the preferred embodiment has a rectangular cross section with dimensions of about 0.508 mm (0.02 inch) by about 0.762 mm (0.03 inch), wires having other shapes and sizes may be used without departing from the scope of the present invention.

A peripheral anchor 34 is formed at each end of the frame elements 30. As illustrated in FIG. 1, these anchors 34 are used to attach the frame 20 between the plurality of cusps C of the damaged valve (e.g., the mitral valve M) in a position between an upstream region and a downstream region. Although other conventional anchor formations may be used without departing from the scope of the present invention, the anchors 34 of the preferred embodiment are hooks. It is envisioned the anchors 34 may also include conventional barbs (not shown) for preventing the hooks from being dislodged from the heart H after implantation. Further, as illustrated in FIG. 2, in the most preferred embodiment the hooks form an angle B of between about 55 degrees and about 80 degrees with the ends of the frame elements 30. In addition, the frame 20 includes a central portion, generally designated by 36, located between the plurality of peripheral anchors 34.

Figure 5:
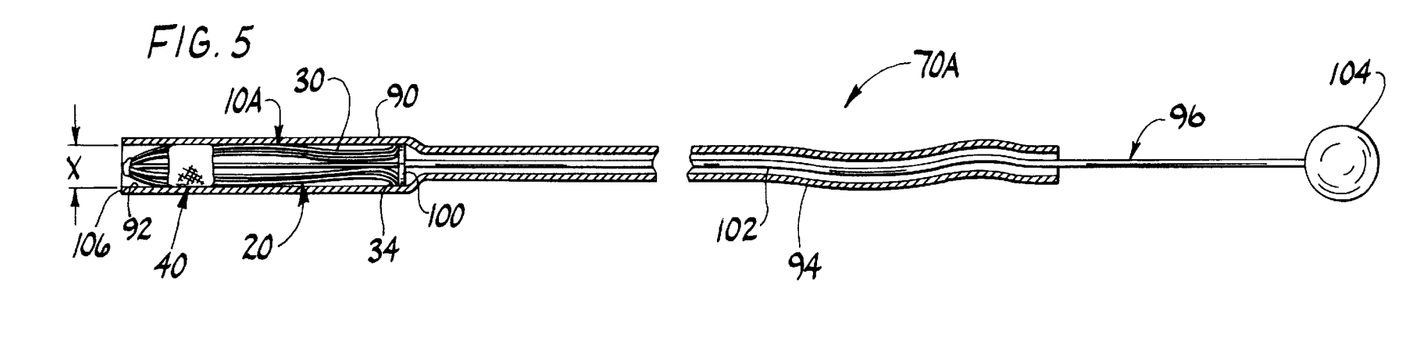
FIG. 5 is a vertical cross section of an introducer for implanting a valve using a transluminal procedure of the present invention.

As further shown in FIG. 2, a band, generally designated by 40, extends around the frame 20 between each of the frame elements 30. The band 40 extends between each frame element 30 and an adjacent frame element to limit maximum spacing S between the frame elements. The band 40 permits the frame elements 30 to be pushed together so the flexibly resilient frame 20 can be collapsed to a collapsed configuration as shown in FIGS. 4 and 5. Depending upon the procedure which is intended to be used when implanting the valve, the frame 20 collapses to configurations having different maximum widths X. For instance, if the artificial valve (e.g., 10M) is implanted using endothoracoscopic methods, the maximum width X is less than about 18 mm and more preferably between about 12 mm and about 18 mm. However, if the valve (e.g., the artificial valve 10A) is implanted through a blood vessel, the maximum width X must be smaller. For instance, the maximum width X must be about 6 mm or more preferably between about 4 mm and about 6 mm. Thus, the frame 20 is sized and shaped for insertion between the plurality of cusps C of the damaged heart valve in a position between an upstream region and a downstream region. Further, because the frame 20 is resilient, it expands to an expanded configuration as shown in FIG. 2 when not collapsed. When in the expanded configuration, the frame 20 has different sizes depending upon which native valve it is intended to replace. For instance, if the artificial valve is intended to repair a damaged mitral valve M or a tricuspid valve, the opposite ends of the frame elements 30 are spaced by a distance D of between about 3 cm and about 5 cm. If the artificial valve is intended to repair a damaged aortic valve A or a pulmonary valve, preferably the opposite ends of the frame elements 30 are spaced by a distance D of between about 2 cm and about 3 cm.

Although the band 40 may be made of other materials, such as heterologous animal pericardium (e.g., bovine or porcine pericardium) or autologous tissue engineered substrates, without departing from the scope of the present invention, the band of the preferred embodiment is made of a biocompatible, radiopaque, elastic material such as silicone rubber, polyurethane or ePTFE. Further, although the band 40 may have other constructions without departing from the scope of the present invention, the band of the preferred embodiment comprises an internal strip 42 and an external strip 44 joined in face-to-face relation. Although the band 40 may be attached to the frame elements 30 by other means, in the most preferred embodiment, the internal and external strips 42, 44, respectively, are adhesively bonded to the frame elements and to each other. Further, although the band 40 illustrated in FIG. 2 is substantially cylindrical, it is envisioned the band may have other shapes without departing from the scope of the present invention. For example, it is envisioned the band 40 may include a rim or flange (not shown) surrounding the valve adjacent the hooks for engaging the cusps C. It is also envisioned that an exterior surface of the band 40 may include a continuous or interrupted sheath of Dacron® velour material, porous PTFE felt or the like to provide sites for vascular connective tissue ingrowth to enhance stability of the device after its implantation. (Dacron is a U.S. federally registered trademark of E.I. duPont de Nemours and Company of Wilmington Del.)

The flexible valve element 22 is disposed within the frame 20 and attached to the central portion 36 of the frame. The valve element 22 has a convex upstream side 50 facing an upstream region (e.g., the left atrium LA) when the frame 20 is anchored between the cusps C of the damaged heart valve (e.g., mitral valve M) in a position between the upstream region and a downstream region; and a concave downstream side 52 opposite the upstream side facing the downstream region (e.g., the left ventricle LV) when the frame 20 is anchored between the cusps of the damaged heart valve in a position between the upstream region and the downstream region. The valve element 22 moves in response to differences between fluid pressure in the upstream region and the downstream region between an open position (as shown in phantom lines in FIG. 3) and a closed position (as shown in solid lines in FIG. 3). When the valve element 22 is in the open position, it permits flow between the upstream region and the downstream region. When in the closed position, the element 22 blocks flow between the upstream and downstream regions. The valve element 22 moves to the open position when fluid pressure in the upstream region is greater than fluid pressure in the downstream region to permit downstream flow from the upstream region to the downstream region. The valve element 22 moves to the closed position when fluid pressure in the downstream region is greater than fluid pressure in the upstream region to prevent flow reversal from the downstream region to the upstream region. Although the valve element 22 may be made of other materials without departing from the scope of the present invention, the valve element of the preferred embodiment is made of a biocompatible elastic material such as silicone rubber, polyurethane, ePTFE, heterologous animal pericardium (e.g., bovine or porcine pericardium), or autologous tissue engineered substrates. Further, although the valve element 22 may have other thicknesses without departing from the scope of the present invention, the valve element of the preferred embodiment has a thickness of between about 0.127 mm (0.005 inch) and about 0.381 mm (0.015 inch). In addition, it is envisioned the valve element 22 may be longitudinally pleated without departing from the scope of the present invention. Without wishing to be bound by any particular theory, it is envisioned that longitudinal pleats may encourage laminar flow through the valve when in the open position.

The upstream side 50 of the flexible valve element 22 has an apex 54 which is attached to the frame 20 at the junction 32 of the elements 30. As illustrated in FIG. 3, the flexible valve element 22 is attached to the central portion 36 of the frame 20 at a position substantially centered between the anchors 34. Although the valve element 22 may be attached to the frame 20 by other means without departing from the scope of the present invention, the valve element of the preferred embodiment is attached to the frame by adhesive bonding. Further, the flexible valve element 22 is attached to the frame 20, and more particularly to the band 40, at several attachment points 56 around the frame. Thus, the valve element 22 forms flaps 58 extending between adjacent attachment points 56. Each of the flaps 58 and a corresponding portion of the band 40 extending between adjacent attachment points 56 defines an opening 60 through the valve when the valve element 22 moves to the open position. Although the valve element 22 may be attached to the band 40 using other means, the valve element of the preferred embodiment is attached to the band by adhesive bonding.

As illustrated in FIGS. 4 and 5, the artificial valves 10M, 10A, respectively, are used in combination with instruments, generally designated by 70M, 70A, for inserting the artificial valve between the cusps C of damaged heart valves M, A. The instrument 70M shown in FIG. 4 is intended for use when implanting the valve 10M using an endothoracoscopic procedure. It is envisioned this instrument would be used primarily when implanting an artificial valve in the mitral valve M, however similar instruments could be used to implant artificial valves in other native valves of the heart H such as the tricuspid valve. When used to implant an artificial valve in a tricuspid valve, the instrument could be introduced through a jugular vein. The endothoracoscopic instrument 70M comprises a tubular holder 72, and an elongate tubular manipulator 74 attached to the holder for manipulating the holder into position. Further, the instrument 70M includes an ejector, generally designated by 76, positioned in a hollow interior 78 of the holder 72 for ejecting the artificial heart valve 10M from the holder. The hollow interior 78 of the holder 72 is sized for holding the artificial valve 10M when the frame 20 is in the collapsed configuration (e.g., less than 18 mm). Further, the hollow interior 78 may have axial grooves (not shown) for receiving the anchors 34 of the valve to prevent the anchors from being tangled during valve implantation. The manipulator 74 is a semi-rigid tube attached to the holder 72 for manipulating the holder through an incision made in the heart and into position adjacent the plurality of cusps C of the damaged heart valve. The ejector 76 includes a flat plunger tip 80 which engages the valve 10M, a push rod 82 attached to the tip for moving the tip forward in the holder 72 for ejecting the valve from the holder, and a handle 84 attached to the push rod opposite the plunger tip for gripping the ejector when ejecting the valve from the holder.

To implant an artificial valve 10M using the endothoracoscopic instrument 70M, a small opening is made in a chest wall of a patient and a small incision is made in a heart of the patient. The holder end 86 of the instrument 70M is inserted through the opening made in the chest wall and the incision made in the heart. The inserted end 86 of the instrument 70M is positioned adjacent the cusps C of the damaged heart valve M and the artificial valve 10M is ejected from the end of the instrument into a position between the cusps of the damaged valve as shown in FIG. 1. When ejecting the valve 10M from the end 86 of the instrument 70M, it is envisioned that the handle 84 of the ejector 76 will be held in place while the manipulator 74 and holder 72 are withdrawn to push the valve out of the holder. Once the valve 10M is in position, the instrument 70M is withdrawn from the chest before the opening and incision are closed using conventional procedures. As will be appreciated by those skilled in the art, the valve 10M may be implanted using this procedure with minimal trauma to the heart and without removing the damaged heart valve from the heart.

The instrument 70A shown in FIG. 5 is intended for use when implanting the valve 10A by a transluminal procedure through a vessel. It is envisioned this instrument 70A would be used when implanting an artificial valve in the pulmonary valve or the aortic valve. When used to implant an artificial valve in a pulmonary valve, the instrument could be introduced through a jugular vein, and when used to implant an artificial valve in an aortic valve, the instrument could be introduced through a femoral artery. The instrument 70A comprises a holder 90 having a hollow interior 92 sized for holding the artificial valve 10A when the frame is in the collapsed configuration (e.g., less than 6 mm) and an elongate flexible manipulator 94 attached to the holder for manipulating the holder through a vessel and into position adjacent the plurality of cusps C of the damaged heart valve A. Further, the instrument 70A has a flexible ejector, generally designated by 96, mounted in the hollow interior 92 of the holder 90 for ejecting the artificial heart valve 10A from the hollow interior of the holder into position between the cusps C of the damaged heart valve A. The manipulator 94 is used to manipulate the instrument 70A through the vessel. The ejector 96 includes a flat plunger tip 100 which engages the valve 10A, a push rod 102 attached to the tip for moving the tip forward in the holder 90 for ejecting the valve from the holder, and a handle 104 attached to the push rod opposite the plunger tip for gripping the ejector when ejecting the valve from the holder. In contrast to the manipulator 74 of the endothorascopic instrument 70M, the manipulator 94 of the transluminal instrument 70A is longer and flexible so it can be pushed or pulled through a vessel and/or over a conventional guide wire (not shown).

In an alternate embodiment (not shown), it is envisioned that the apex 54 of the flexible valve element 22 and the junction 32 of the frame elements 30 may include an opening to allow the guide wire to pass through the valve. Although this opening may have other dimensions without departing from the scope of the present invention, in one embodiment the opening has a diameter of between about 0.5 mm and about 1 mm. After removal of the guide wire, it is envisioned that this opening may provide surface washing to reduce a potential for blood to coagulate adjacent the downstream side of the valve element 22. It is further envisioned that an opening may be used even where a guide wire is not needed to reduce potential for blood to coagulate adjacent the valve element 22.

To implant an artificial valve 10A using the transluminal instrument 70A, a small incision is made in a vessel (e.g., the femoral artery) leading to a heart H. An end 106 of the instrument 70A having the holder 90 is inserted through the incision made in the vessel and the end is pushed through the vessel and over a guide wire until the end is adjacent the cusps C of the damaged heart valve A. Once in position, the artificial valve 10A is ejected from the end 106 of the instrument 70A between the cusps C of the damaged heart valve A. As with the endothorascopic procedure described above, the transluminal procedure may be performed with minimal trauma to the heart and without removing the damaged heart valve from the heart and without cardiopulmonary bypass or heart arrest.

Figure 6:
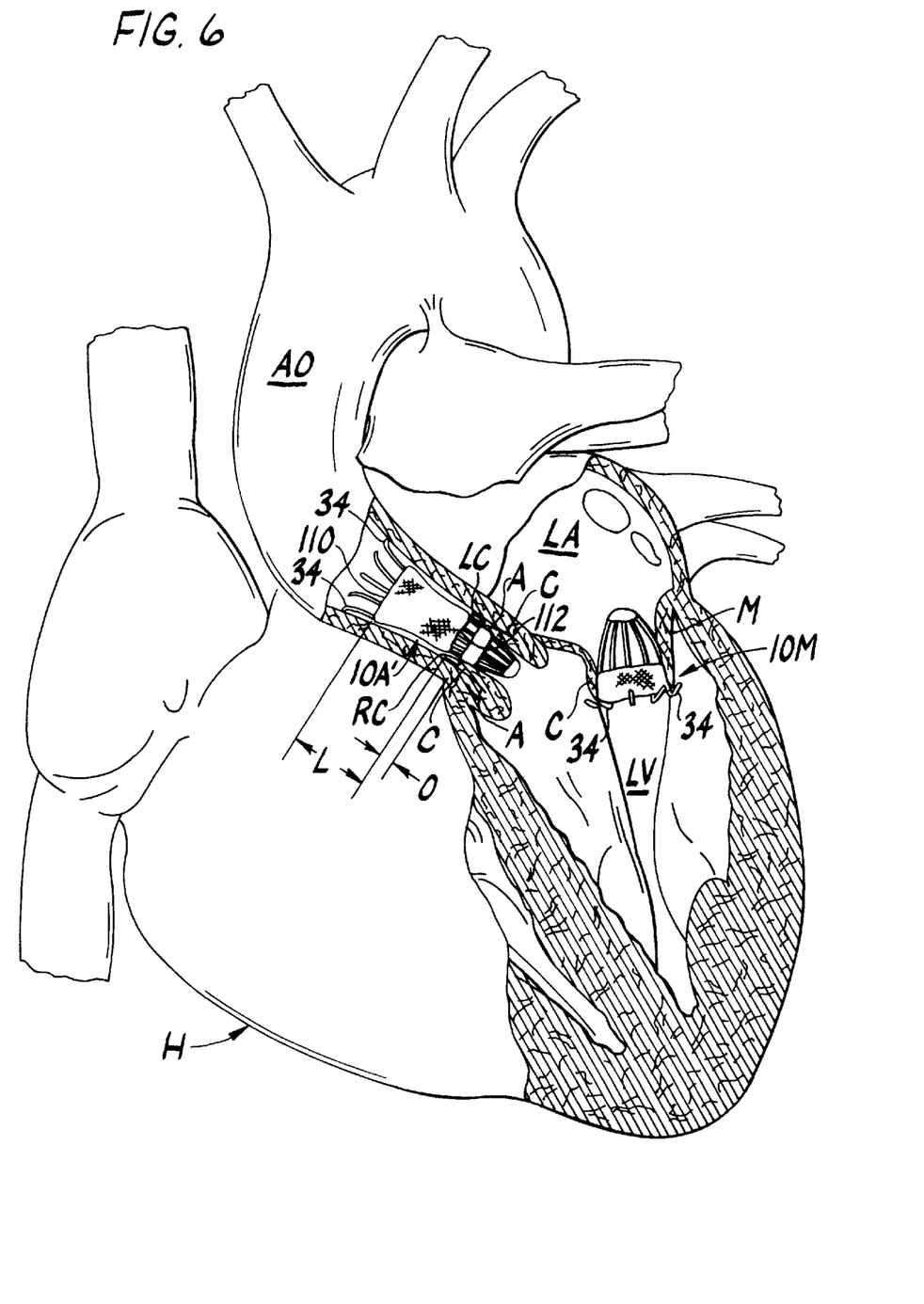
FIG. 6 is a front elevation of a heart in partial section showing artificial valves of the present invention.

A second embodiment of the aortic valve is generally designated by 10A' in FIG. 6. This second embodiment is identical to the aortic valve of the first embodiment except that it includes a second band 110 surrounding the frame 20 downstream from the first band 40. The second band 110 permits the frame elements 30 to be pushed together so the frame 20 can be collapsed to the collapsed configuration, but limits the maximum spacing between adjacent frame elements. It is envisioned that the second band 110 may be constructed similarly to the first band 40 and may be made from similar materials to the first band. As will be appreciated by those skilled in the art, the second band 100 of the aortic valve 10A' supports the tissue surrounding the downstream region (i.e., the ascending aorta) and prevents the tissue from distending. An opening 112 provided between the first and second bands 40, 110, respectively, corresponds to openings of the right and left coronary arteries (designated by RC, LC, respectively) which enter the aorta immediately above the cusps of the native valve so the replacement valve does not obstruct blood flow through these openings. Although the opening 112 may have other widths O without departing from the scope of the present invention, in one embodiment the opening has a width of between about 5 mm and about 1 cm. Although the second band 110 may have other lengths L without departing from the scope of the present invention, in one embodiment the second band 110 has a length of between about 6 cm and about 12 cm. It is further envisioned that hooks (not shown) may be provided along the frame elements 30 adjacent the second band 110 to engage the tissue to further prevent distention of the tissue.

As will be appreciated by those skilled in the art, the valves and instruments described above permit "beating heart" procedures (i.e., without cardiopulmonary bypass or cardioplegic arrest) in part due to the relatively small size of the valves and instruments. Further, the valves described above permit implantation without removal of the native valves. The valves also permit some correction of valvular stenosis along with correction of regurgitant valvular disease. It is further envisioned that the valves described above may be coated with heparin or other protective coatings and immune suppressant coatings (e.g., rapamycin coating) to reduce coagulation or immune inflammatory response initiation.

It is envisioned that the valves of the present invention may be suitable for implant in pediatric patients due to their small size and substantially unrestricted flow characteristics. Further, because the valves adaptively expand, they are capable of expanding to fit the growing child.

It is further envisioned that rapidly implanting the valves of the present invention using an endothoracoscopic technique may provide a suitable remedy of acute papillary muscle dysfunction due to major chordal rupture or frank papillary muscle infarction.

In heavily calcified native valves, implantation of the valve described above could remedy regurgitant disease without disturbing the calcific deposits.

When used in the mitral site, the valve described above avoids problems associated with valve cusp stents and fabric arms present in prior art bioprosthetic valves. Also use of the valve described above at the mitral site eliminates removal of or damage to papillary muscles and most of the chordae tendinae thereby preserving systolic apical movement. Still further, the valve described above is compliant and capable of regurgitant control in cases of ischemic mitral regurgitation.

When used in the aortic valve site, placement of the valve may be controlled using fluoroscopic guidance to ensure the native cusps are positioned in the valve sinuses and the coronary openings above the valve site are not obstructed. It is envisioned that a conventional dye injection technique may be used to identify the coronary openings.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An artificial valve for repairing a damaged heart valve having a plurality of cusps separating an upstream region from a downstream region, said artificial valve comprising:
   a flexibly resilient frame sized and shaped for insertion in a position between the upstream region and the downstream region, the frame having a plurality of peripheral anchors for anchoring the frame in the position between the upstream region and the downstream region and a central portion located between the plurality of peripheral anchors;
   a band attached to the frame limiting spacing between adjacent anchors of said plurality of peripheral anchors; and
   a flexible valve element attached to the central portion of the frame and adjacent the band, said valve element being substantially free of connections to the frame except at the central portion of the frame and adjacent the band, said valve element having an upstream side facing said upstream region when the frame is anchored in the position between the upstream region and the downstream region and a downstream side opposite the upstream side facing said downstream region when the frame is anchored in the position between the upstream region and the downstream region, said valve element moving in response to a difference between fluid pressure in said upstream region and fluid pressure in said downstream region between an open position in which the element permits downstream flow between said upstream region and said downstream region and a closed position in which the element blocks flow reversal from said downstream region to said upstream region, wherein the valve element moves to the open position when fluid pressure in said upstream region is greater than fluid pressure in said downstream region to permit downstream flow from said upstream region to said downstream region and the valve element moves to the closed position when fluid pressure in said downstream region is greater than fluid pressure in said upstream region to prevent flow reversal from said downstream region to said upstream region.

2. An artificial valve as set forth in claim 1 wherein said flexibly resilient frame is collapsible to a configuration having a maximum width less than about 18 mm.

3. An artificial valve as set forth in claim 2 wherein said flexibly resilient frame is collapsible to a configuration having a maximum width between about 12 mm and about 18 mm.

4. An artificial valve as set forth in claim 2 wherein said flexibly resilient frame is collapsible to a configuration having a maximum width less than about 6 mm.

5. An artificial valve as set forth in claim 4 wherein said flexibly resilient frame is collapsible to a configuration having a maximum width between about 4 mm and about 6 mm.

6. An artificial valve as set forth in claim 1 wherein said flexible valve element is attached to the central portion of the frame at a position substantially centered between said plurality of anchors.

7. An artificial valve as set forth in claim 6 wherein said flexible valve element is attached to the frame at a plurality of attachment points around the frame thereby forming flaps, each of said flaps extending between adjacent attachment points of said plurality of attachment points and at least partially defining an opening through the valve when the valve element moves to the open position.

8. An artificial valve as set forth in claim 1 wherein said flexibly resilient frame comprises a plurality of U-shaped elements joined together at a junction of the elements.

9. An artificial valve as set forth in claim 8 wherein said upstream side of the flexible valve element is convex and has an apex which is attached to the frame at the junction of the elements.

10. An artificial valve for repairing a damaged heart valve having a plurality of cusps separating an upstream region from a downstream region, said artificial valve comprising:

a flexibly resilient frame sized and shaped for insertion in a position between the upstream region and the downstream region, the frame having a plurality of peripheral anchors for anchoring the frame in the position between the upstream region and the downstream region;

a band comprising an internal strip positioned inside and attached to the frame limiting spacing between adjacent anchors of said plurality of peripheral anchors; and a flexible valve element positioned inside the band and attached to the frame, said valve element having a convex upstream side facing said upstream region when the frame is anchored in the position between the upstream region and the downstream region and a concave downstream side opposite the upstream side facing said downstream region when the frame is anchored in the position between the upstream region and the downstream region, said valve element moving in response to a difference between fluid pressure in said upstream region and fluid pressure in said downstream region between an open position in which the element permits downstream flow between said upstream region and said downstream region and a closed position in which the convex side of the element engages the internal strip of the band so the element blocks flow reversal from said downstream region to said upstream region, wherein the valve element moves to the open position when fluid pressure in said upstream region is greater than fluid pressure in said downstream region to permit downstream flow from said upstream region to said downstream region and the valve element moves to the closed position when fluid pressure in said downstream region is greater than fluid pressure in said upstream region to prevent flow reversal from said downstream region to said upstream region.

11. An artificial valve as set forth in claim 10 wherein said flexibly resilient frame is collapsible to a configuration having a maximum width less than about 18 mm.

12. An artificial valve as set forth in claim 11 wherein said flexibly resilient frame is collapsible to a configuration having a maximum width less than about 6 mm.

13. An artificial valve as set forth in claim 10 wherein said flexibly resilient frame comprises a plurality of U-shaped elements having opposite ends, said elements being joined together generally midway between their respective ends at a junction of the elements.

14. An artificial valve as set forth in claim 13 wherein said convex upstream side of the flexible valve element has an apex which is attached to the frame at the junction of the elements.

15. An artificial valve as set forth in claim 10 wherein said band further comprises an external strip, and wherein the internal strip and the external strip are joined in face-to-face relation.

16. An artificial valve as set forth in claim 10 wherein said band is radiopaque.

17. An artificial valve for repairing a damaged heart valve having a plurality of cusps separating an upstream region from a downstream region, said artificial valve comprising:

a flexibly resilient frame sized and shaped for insertion in a position between the upstream region and the downstream region;

a first band surrounding and attached to the frame;

a second band surrounding and attached to the frame downstream from said first band for supporting tissue defining said downstream region to reenforce said tissue and prevent distention thereof; and a flexible valve element attached to the frame having a convex upstream side facing said upstream region when the frame is anchored in the position between the upstream region and tie downstream region and a concave downstream side opposite the upstream side facing said downstream region when the frame is anchored in the position between the upstream region and the downstream region, said valve clement moving in response to a difference between fluid pressure in said upstream region and fluid pressure in said downstream region between an open position in which the element permits downstream flow between said upstream region and said downstream region and a closed position in which the element blocks flow reversal from said downstream region to said upstream region, wherein the valve element moves to the open position when fluid pressure in said upstream region is greater than fluid pressure in said downstream region to permit downstream flow from said upstream region to said downstream region and the valve element moves to the closed position when fluid pressure in said downstream region is greater than fluid pressure in said upstream region to prevent flow reversal from said downstream region to said upstream region.

18. An artificial valve for repairing a damaged heart valve having a plurality of cusps separating an upstream region from a downstream region, said artificial valve comprising:

a plurality of U-shaped frame elements sized and shaped for insertion in the heart in a position between the upstream region and the downstream region, each of said plurality of frame elements having opposite ends, said elements being joined together generally midway between their respective ends at a junction of the elements;

a band surrounding the frame and extending between adjacent elements of said plurality of frame elements to limit spacing between said adjacent elements; and a flexible valve element attached to the junction of the frame elements having a convex upstream side facing said upstream region when said plurality of frame elements is inserted in the position between the upstream region and the downstream region and a concave downstream side opposite the upstream side facing said downstream region when said plurality of frame elements is inserted in the position between the upstream region and the downstream region, said valve element moving in response to a difference between fluid pressure in said upstream region and fluid pressure in said downstream region between an open position in which the element permits downstream flow between said upstream region and said downstream region and a closed position in which the element blocks flow reversal from said downstream region to said upstream region, wherein the valve element moves to the open position when fluid pressure in said upstream region is greater than fluid pressure in said downstream region to permit downstream flow from said upstream region to said downstream region and the valve element moves to the closed position when fluid pressure in said downstream region is greater than fluid pressure in said upstream region to prevent flow reversal from said downstream region to said upstream region.

19. An artificial valve as set forth in claim 18 wherein each end of said plurality of frame elements has an anchor for anchoring the respective frame element in the position between the upstream region and the downstream region.

20. An artificial valve as set forth in claim 19 wherein each of said anchors comprises a hook for anchoring the respective frame element in the position between the upstream region and the downstream region.

21. An artificial valve as set forth in claim 18 wherein each of said frame elements is flexibly resilient and collapsible to a configuration having a maximum width less than about 18 mm.

22. An artificial valve as set forth in claim 21 wherein each of said frame elements is collapsible to a configuration having a maximum width less than about 6 mm.

23. An artificial valve as set forth in claim 18 wherein said band comprises an internal strip and an external strip joined in face-to-face relation.

24. An artificial valve as set forth in claim 18 wherein said flexible valve element is attached to the band at a plurality of attachment points around the band thereby forming flaps extending between adjacent attachment points of said plurality of attachment points, and wherein each of said flaps and a corresponding portion of the band define an opening through the valve when the valve element moves to the open position.

25. An artificial valve as set forth in claim 18 wherein each of said frame elements has a distance between its respective opposite ends of between about 3 cm and about 5 cm.

26. An artificial valve as set forth in claim 18 wherein each of said frame elements has a distance between its respective opposite ends of between about 2 cm and about 3 cm.

27. An artificial valve as set forth in claim 18 wherein said band is a first band and said artificial valve further comprises a second band surrounding the frame downstream from said first band for supporting tissue defining said downstream region to reenforce said tissue and prevent distention thereof.

28. In combination, an artificial valve for repairing a damaged heart valve having a plurality of cusps separating an upstream region from a downstream region, and an instrument for inserting the artificial valve between the upstream region and the downstream region, said combination comprising:
  an artificial valve including
    a flexibly resilient frame sized and shaped for insertion between the upstream region and the downstream region, the frame having a plurality of peripheral anchors for anchoring the frame between the upstream region and the downstream region and a central portion located between the plurality of peripheral anchors, the frame being collapsible to a configuration having a maximum width less than about 18 mm,
    a band attached to the frame limiting spacing between adjacent anchors of said plurality of peripheral anchors, and
    a flexible valve element attached to the central portion of the frame and adjacent the band, said valve element being substantially free of connections to the frame except at the central portion of the frame and adjacent the band, said valve element having an upstream side facing said upstream region when the frame is anchored between the upstream region and the downstream region and a downstream side opposite the upstream side facing said downstream region when the frame is anchored between the upstream region and the downstream region, said valve element moving in response to a difference between fluid pressure in said upstream region and fluid pressure in said downstream region between an open position in which the element permits downstream flow between said upstream region and said downstream region and a closed position in which the element blocks flow reversal from said downstream region to said upstream region, wherein the valve element moves to the open position when fluid pressure in said upstream region is greater than fluid pressure in said downstream region to permit downstream flow from said upstream region to said downstream region and the valve element moves to the closed position when fluid pressure in said downstream region is greater than fluid pressure in said upstream region to prevent flow reversal from said downstream region to said upstream region; and
  an instrument including
    a holder having a hollow interior sized for holding the artificial valve when the frame is in the collapsed configuration;
    an elongate manipulator attached to the holder for manipulating the holder into position between the upstream region and the downstream region; and
    an ejector mounted in the hollow interior of the holder for ejecting the artificial heart valve from the hollow interior of the holder into position between the upstream region and the downstream region.

29. In combination, an artificial valve for repairing a damaged heart valve having a plurality of cusps separating an upstream region from a downstream region, and an instrument for inserting the artificial valve between the upstream region and the downstream region, said combination comprising:
  an artificial valve including
    a plurality of flexibly resilient U-shaped frame elements sized and shaped for insertion between the upstream region and the downstream region, each of said plurality of frame elements having opposite ends, said elements being joined together generally midway between their respective ends thereby forming a frame having a plurality of peripheral anchors for anchoring the frame between the upstream region and the downstream region, the frame being collapsible to a configuration having a maximum width less than about 18 mm, and a flexible valve element attached to the frame having a convex upstream side facing said upstream region when the frame is anchored between the upstream region and the downstream region and a concave downstream side opposite the upstream side facing said downstream region when the frame is anchored between the upstream region and the downstream region, said valve element moving in response to a difference between fluid pressure in said upstream region and fluid pressure in said downstream region between an open position in which the element permits downstream flow between said upstream region and said downstream region and a closed position in which the element blocks flow reversal from said downstream region to said upstream region, wherein the valve element moves to the open position when fluid pressure in said upstream region is greater than fluid pressure in said downstream region to permit downstream flow from said upstream region to said downstream region and the valve element moves to the closed position when fluid pressure in said downstream region is greater than fluid pressure in said upstream region to prevent flow reversal from said downstream region to said upstream region; and an instrument including a holder having a hollow interior sized for holding the artificial valve when the frame is in the collapsed configuration, an elongate manipulator attached to the holder for manipulating the holder into position between the upstream region and the downstream region, and an ejector mounted in the hollow interior of the holder for ejecting the artificial heart valve from the hollow interior of the holder into position between the upstream region and the downstream region.

30. An artificial valve for repairing a damaged heart valve having a plurality of cusps separating an upstream region from a downstream region, said artificial valve comprising:

a flexibly resilient frame sized and shaped for insertion in a position between the upstream region and the downstream region;

a first band surrounding the frame;

a second band surrounding the frame downstream from said first band for supporting tissue defining said downstream region to reenforce said tissue and prevent distention thereof; and a flexible valve element attached to a central portion of the frame having an upstream side facing said upstream region when the frame is anchored in the position between the upstream region and the downstream region and a downstream side opposite the upstream side facing said downstream region when the frame is anchored in the position between the upstream region and the downstream region, said valve element moving relative to the frame in response to a difference between fluid pressure in said upstream region and fluid pressure in said downstream region between an open position in which the element permits downstream flow between said upstream region and said downstream region and a closed position in which the element blocks flow reversal from said downstream region to said upstream region, wherein the valve element moves to the open position when fluid pressure in said upstream region is greater than fluid pressure in said downstream region to permit downstream flow from said upstream region to said downstream region and the valve element moves to the closed position when fluid pressure in said downstream region is greater than fluid pressure in said upstream region to prevent flow reversal from said downstream region to said upstream region.

* * * * *